United States Patent
Mahadevan et al.

(10) Patent No.: US 10,960,158 B2
(45) Date of Patent: Mar. 30, 2021

(54) PORTABLE HANDHELD PRESSURE SUPPORT SYSTEM AND METHOD

(71) Applicant: KONINKLIJKE PHILIPS N.V., Eindhoven (NL)

(72) Inventors: Anandi Mahadevan, Murrysville, PA (US); Laurent Brouqueyre, Kennesaw, GA (US); Christopher Scott Lucci, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1288 days.

(21) Appl. No.: 14/395,832

(22) PCT Filed: Apr. 23, 2013

(86) PCT No.: PCT/IB2013/053187
§ 371 (c)(1),
(2) Date: Oct. 21, 2014

(87) PCT Pub. No.: WO2013/160822
PCT Pub. Date: Oct. 31, 2013

(65) Prior Publication Data
US 2015/0128947 A1    May 14, 2015

Related U.S. Application Data

(60) Provisional application No. 61/637,586, filed on Apr. 24, 2012.

(51) Int. Cl.
*A61M 16/00* (2006.01)
*A61M 16/20* (2006.01)
(Continued)

(52) U.S. Cl.
CPC ........ *A61M 16/0066* (2013.01); *A61M 16/00* (2013.01); *A61M 16/0003* (2014.02);
(Continued)

(58) Field of Classification Search
CPC .......... A61M 16/0066; A61M 16/0003; A61M 16/0069; A61M 16/161; A61M 16/201;
(Continued)

(56) References Cited

U.S. PATENT DOCUMENTS 5,211,171 A * 5/1993 Choromokos ...... A61M 1/0066
                                                    128/205.19
5,363,842 A * 11/1994 Mishelevich ........ A61B 8/0875
                                                    128/200.14
(Continued)

FOREIGN PATENT DOCUMENTS

CN 101193676 A 6/2008
CN 102333505 A 1/2012
(Continued)

*Primary Examiner* — Kendra D Carter
*Assistant Examiner* — Elliot S Ruddie (57) ABSTRACT

The present disclosure pertains to a portable handheld pressure support system configured to deliver a pressurized flow of breathable gas to the airway of a subject. The pressure support system is configured to treat COPD and/or other patients suffering from dyspnea and/or other conditions. The pressure support system is configured to be small and lightweight so that a subject may carry the system and use the system as needed without requiring a device to be worn on the face. The present disclosure contemplates that the portable handheld pressure support system may be used to treat symptoms and/or conditions related to dyspnea, and/or for other uses. In one embodiment, the system comprises one or more of a pressure generator, a subject interface, one or more sensors, one or more processors, a user interface, electronic storage, a portable power source, a housing, a handle, and/or other components.

24 Claims, 3 Drawing Sheets

(51) Int. Cl.
*A61M 16/16* (2006.01)
*A61M 16/06* (2006.01)
*A61M 16/10* (2006.01)

(52) U.S. Cl.
CPC .... *A61M 16/0051* (2013.01); *A61M 16/0069* (2014.02); *A61M 16/0666* (2013.01); *A61M 16/161* (2014.02); *A61M 16/201* (2014.02); *A61M 16/205* (2014.02); *A61M 16/0006* (2014.02); *A61M 16/0072* (2013.01); *A61M 16/0075* (2013.01); *A61M 16/1055* (2013.01); *A61M 2016/0039* (2013.01); *A61M 2205/18* (2013.01); *A61M 2205/3317* (2013.01); *A61M 2205/3365* (2013.01); *A61M 2205/3368* (2013.01); *A61M 2205/35* (2013.01); *A61M 2205/50* (2013.01); *A61M 2205/505* (2013.01); *A61M 2205/586* (2013.01); *A61M 2205/8206* (2013.01); *A61M 2205/8237* (2013.01)

(58) Field of Classification Search
CPC ................ A61M 16/205; A61M 16/00; A61M 16/0051; A61M 16/0666; A61M 16/0006; A61M 16/0072; A61M 16/0075; A61M 16/1055; A61M 2016/0039; A61M 2205/18; A61M 2205/3317; A61M 2205/3368; A61M 2205/35; A61M 2205/50; A61M 2205/505; A61M 2205/586; A61M 2205/3365; A61M 2205/8206; A61M 2205/8237
See application file for complete search history.

(56) References Cited

U.S. PATENT DOCUMENTS

| | | |
|---|---|---|
| 5,398,676 A | 3/1995 | Press |
| 6,012,450 A | 1/2000 | Rubsamen |
| 6,349,724 B1* | 2/2002 | Burton ............. A61M 16/0057 128/204.18 |
| 7,051,731 B1* | 5/2006 | Rogerson ............ A61M 15/009 128/200.23 |
| 7,219,664 B2 | 5/2007 | Ruckdeschel |
| 9,027,553 B2 | 5/2015 | Witt |
| 9,314,579 B2 | 4/2016 | McDaniel |
| 2004/0223917 A1 | 11/2004 | Hindle |
| 2004/0249300 A1 | 12/2004 | Miller |
| 2005/0051168 A1* | 3/2005 | DeVries ............ A61M 16/0051 128/204.21 |
| 2008/0041383 A1* | 2/2008 | Matthews ........... A61M 16/026 16/26 |
| 2009/0156952 A1 | 6/2009 | Hunter |
| 2010/0292544 A1* | 11/2010 | Sherman .................. A61B 5/00 600/300 |
| 2010/0312575 A1* | 12/2010 | Witt .................... A61M 16/024 705/2 |
| 2011/0203587 A1 | 8/2011 | Bertinetti |
| 2012/0060838 A1 | 3/2012 | Laura Lapoint |
| 2014/0007878 A1* | 1/2014 | Armitstead ............ A61B 5/083 128/204.23 |
| 2014/0102454 A1* | 4/2014 | Paul .................. A61M 16/0051 128/204.23 |

FOREIGN PATENT DOCUMENTS

| | | |
|---|---|---|
| JP | 2005198690 A | 7/2005 |
| JP | 2012505691 A | 3/2012 |
| RU | 2338457 C2 | 1/2006 |
| RU | 2447871 C2 | 4/2012 |
| WO | WO0149349 A1 | 7/2001 |
| WO | WO2004032719 A2 | 4/2004 |
| WO | WO2010044038 A2 | 4/2010 |
| WO | 2010133986 A1 | 11/2010 |
| WO | WO2012174602 A1 | 12/2012 |

* cited by examiner

PORTABLE HANDHELD PRESSURE SUPPORT SYSTEM AND METHOD

CROSS REFERENCE TO RELATED APPLICATIONS

This patent application claims the priority benefit under 35 U.S.C. § 371 of international patent application no. PCT/IB2013/053187, filed Apr. 23, 2013, which claims the the priority benefit under 35 U.S.C. § 119(e) of U.S. Provisional Application No. 61/637,586 filed on Apr. 24, 2012, the contents of which are herein incorporated by reference.

BACKGROUND OF THE INVENTION

1. Field of the Invention

The present disclosure pertains to a portable handheld pressure support system configured to deliver a pressurized flow of breathable gas to the airway of a subject.

2. Description of the Related Art

It is well known to apply a positive air pressure (PAP) to a patient's airway to keep the airway open and avoid collapse during breathing. This positive pressure effectively "splints" the airway, thereby maintaining an open passage to the lungs. Dyspnea, or shortness of breath, is a primary symptom of COPD. COPD patients suffer occurrences of dyspnea when exerting themselves. The forms of exertion may include performing household chores, walking to the local store, or climbing a set of stairs. An onset of dyspnea limits a patient's ability to perform activities and can trigger apprehension or panic, further reducing the patient's ability to function. COPD patients carry short acting bronchodilators to alleviate their symptoms of dyspnea. Bronchodilators have drawbacks including that they are steroid based, they are slow acting (4-20 minutes), they are effective for only asthmatic-based symptoms, and they rely on expensive pharmaceuticals.

SUMMARY OF THE INVENTION

Accordingly, one or more aspects of the present disclosure relate to a portable handheld pressure support system configured to deliver a pressurized flow of breathable gas to the airway of a subject. The pressure support system comprises a pressure generator, a subject interface, one or more sensors, one or more processors, a portable power source, a housing, and a handle. The pressure generator is configured to generate the pressurized flow of breathable gas. The subject interface is configured to communicate the pressurized flow of breathable gas to the airway of the subject. The one or more sensors are configured to generate output signals conveying information related to one or more gas parameters of the pressurized flow of breathable gas. The one or more processors are configured to control operation of the pressure generator to generate the pressurized flow of breathable gas based on the output signals from the one or more sensors, according to a positive pressure support therapy regime. The portable power source is configured to power the pressure generator, the one or more sensors, and the one or more processors. The housing is configured to contain the pressure generator, the subject interface, the one or more sensors, the one or more processors, and the power source. The handle is attached to and/or formed by the housing and is configured to be grasped by the subject to hold the housing in position with respect to the airway of the subject as the pressurized flow of breathable gas is delivered to the airway of the subject.

Yet another aspect of the present disclosure relates to a method of delivering a pressurized flow of breathable gas to the airway of a subject with a handheld pressure support system that includes a housing. The housing contains a pressure generator, a subject interface, one or more sensors, one or more processors, and a power source. The housing forms and/or is attached to a handle. The method comprises generating the pressurized flow of breathable gas with the pressure generator; communicating the pressurized flow of breathable gas to the airway of the subject with the subject interface; generating output signals conveying information related to one or more gas parameters of the pressurized flow of breathable gas with the one or more sensors; controlling generation of the pressurized flow of breathable gas with the one or more processors, based on the output signals, according to a positive pressure support therapy regime; portably powering the pressure generator, the one or more sensors, and the one or more processors with the power source; and grasping the handle to hold the housing in position with respect to the airway of the subject as the pressurized flow of breathable gas is delivered to the airway of the subject.

Still another aspect of the present disclosure relates to a portable handheld pressure support system configured to deliver a pressurized flow of breathable gas to the airway of a subject. The pressure support system comprises means for generating the pressurized flow of breathable gas; means for communicating the pressurized flow of breathable gas to the airway of the subject; means for generating output signals conveying information related to one or more gas parameters of the pressurized flow of breathable gas; means for controlling the means to generate the pressurized flow of breathable gas based on the output signals, according to a positive pressure support therapy regime; means for portably powering the means to generate the pressurized flow of breathable gas, the means for generating output signals, and the means for controlling; means for containing the means to generate the pressurized flow of breathable gas, the means for communicating, the means for generating output signals, the means for controlling, and the means for portably powering; and means for engaging the hand of the subject to be grasped by the subject, the means for engaging being connected to and/or formed by the means for containing, the means for engaging being configured to be grasped by the subject to hold the means for containing in position with respect to the airway of the subject as the pressurized flow of breathable gas is delivered to the airway of the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
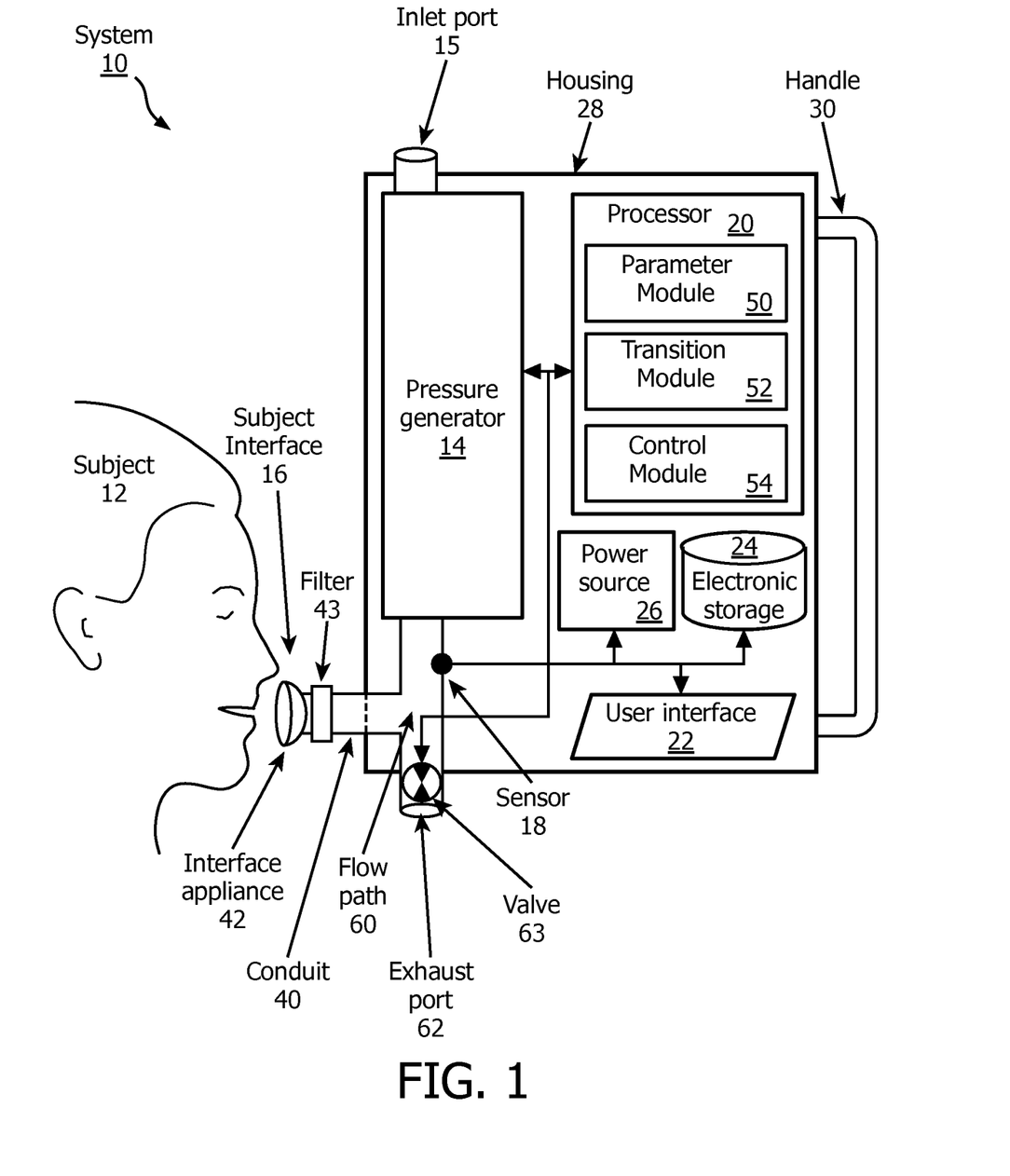
FIG. 1 is a schematic of a portable handheld pressure support system configured to deliver a pressurized flow of breathable gas to the airway of a subject.

FIG. 1 schematically illustrates a portable handheld pressure support system 10 configured to provide pressure support therapy to a subject 12. Pressure support system 10 is configured to provide the pressure support therapy in the form of a pressurized flow of breathable gas that is delivered to the airway of the subject. Pressure support system 10 is configured to treat COPD and/or other patients suffering from dyspnea and/or other conditions. The pressure support therapy provided to dyspnea patients is configured to be used as needed by subject 12 to rapidly alleviate shortness of breath. Pressure support system 10 is configured to be small and lightweight so that subject 12 may carry system 10 and use system 10 as needed without requiring a device to be worn on the face. The present disclosure contemplates that portable handheld pressure support system 10 may be used to treat symptoms and/or conditions related to dyspnea due to COPD, and/or for other uses. The other uses may include, for example, treating dyspnea related to pulmonary cancer, treating emphysema, treating pneumonia, treating Cheyne-Stokes respiration and/or other disordered breathing, improving the exercise capacity of any patient limited by dyspnea, and/or other uses.

In some embodiments, system 10 comprises one or more of a pressure generator 14, a subject interface 16, one or more sensors 18, one or more processors 20, a user interface 22, electronic storage 24, a portable power source 26, a housing 28, a handle 30, and/or other components.

Pressure generator 14 is configured to generate a flow of gas for delivery to the airway of a subject 12. Pressure generator 14 may control one or more parameters of the flow of gas (e.g., flow rate, pressure, volume, temperature, gas composition, etc.) for therapeutic purposes, and/or for other purposes. By way of a non-limiting example, pressure generator 14 may be configured to control the flow rate and/or pressure of the flow of gas to provide pressure support to the airway of subject 12.

Pressure generator 14 receives a flow of gas from a gas source, such as the ambient atmosphere, and elevates the pressure of that gas for delivery to the airway of a patient. In some embodiments, pressure generator 14 receives a flow of gas from a gas source through inlet port 15. Pressure generator 14 is any device, such as, for example, a pump, blower, piston, or bellows, that is capable of elevating the pressure of the received gas for delivery to a patient. Pressure generator 14 may comprise one or more valves for controlling the pressure/flow of gas. The present disclosure also contemplates controlling the operating speed of the blower, either alone or in combination with such valves, to control the pressure/flow of gas provided to the patient.

In some embodiments, pressure generator 14 may be configured to supply a pressurized flow of breathable gas at pressures up to about 40 cm of water. In some embodiments, pressure generator 14 may be configured to supply a pressurized flow of breathable gas at pressures up to about 30 cm of water. In some embodiments, pressure generator 14 may be configured to supply a pressurized flow of breathable gas at pressures up to about 20 cm of water.

Subject interface 16 is configured to communicate the pressurized flow of breathable gas to the airway of subject 12. As such, subject interface 16 comprises conduit 40, interface appliance 42, filter 43, and/or other components. In some embodiments, filter 43 is configured to filter bacteria and/or other materials. Conduit 40 is configured to convey the pressurized flow of gas to interface appliance 42. Interface appliance 42 is configured to deliver the flow of gas to the airway of subject 12. In some embodiments, interface appliance 42 is configured to be non-invasively engaged by the mouth of subject 12. Non-invasive engagement comprises removably engaging one or more external orifices of the airway of subject 12 (e.g., nostrils and/or mouth) to communicate gas between the airway of subject 12 and interface appliance 42.

In some embodiments, interface appliance 42 is removably coupled to conduit 40. Interface appliance 42 may be removed for cleaning and/or for other purposes. In some embodiments, conduit 40 is configured as a mouthpiece to be engaged by the mouth of subject 12.

In some embodiments, other non-invasive interface appliances may be configured as interface appliance 42. Some examples of non-invasive interface appliance 42 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance. In some embodiments, system 10 may be connected to a classical respiratory circuit (e.g., a six foot hose) such that the classical respiratory circuit functions as subject interface 16.

One or more sensors 18 are configured to generate output signals conveying information related to one or more parameters of the gas within system 10. The one or more parameters of the gas within system 10 may comprise gas parameters related to the pressurized flow of breathable gas, breathing parameters related to respiration of subject 12, and/or other parameters. Sensors 18 may comprise one or more sensors that measure such parameters directly (e.g., through fluid communication with the flow of gas in interface appliance 42). Sensors 18 may comprise one or more sensors that generate surrogate output signals related to the one or more parameters indirectly. For example, sensors 18 may comprise one or more sensors configured to generate an output based on an operating parameter of pressure generator 14 (e.g., patient flow and/or pressure estimations from motor current, voltage, rotational velocity, and/or other operating parameters), and/or other sensors.

The one or more gas parameters of the pressurized flow of breathable gas may comprise, for example, one or more of a flow rate, a volume, a pressure, humidity, temperature, acceleration, velocity, and/or other gas parameters. Breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters.

Although sensors 18 are illustrated in FIG. 1 at a single location in system 10, this is not intended to be limiting. Sensors 18 may comprise sensors disposed in a plurality of locations, such as for example, at various locations within (or in communication with) conduit 40, within pressure generator 14, within (or in communication with) interface appliance 42, and/or other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program modules. The one or more computer program modules may comprise one or more of a parameter module 50, a transition module 52, a control module 54, and/or other modules. Processor 20 may be configured to execute modules 50, 52, and/or 54 by software; hardware; firmware; some combination of software, hardware, and/or firmware; and/or other mechanisms for configuring processing capabilities on processor 20.

It should be appreciated that although modules 50, 52, and 54 are illustrated in FIG. 1 as being co-located within a single processing unit, in implementations in which processor 20 comprises multiple processing units, one or more of modules 50, 52, and/or 54 may be located remotely from the other modules. The description of the functionality provided by the different modules 50, 52, and/or 54 described below is for illustrative purposes, and is not intended to be limiting, as any of modules 50, 52, and/or 54 may provide more or less functionality than is described. For example, one or more of modules 50, 52, and/or 54 may be eliminated, and some or all of its functionality may be provided by other modules 50, 52, and/or 54. As another example, processor 20 may be configured to execute one or more additional modules that may perform some or all of the functionality attributed below to one of modules 50, 52, and/or 54.

Parameter module 50 is configured to determine one or more parameters within system 10. The one or more parameters within system 10 may comprise gas parameters related to the pressurized flow of breathable gas, and/or other parameters. Parameter module 50 is configured to determine the one or more parameters based on the output signals of sensors 18. The information determined by parameter module 50 may be used for controlling pressure generator 14, stored in electronic storage 24, and/or used for other uses.

The one or more gas parameters of the pressurized flow of breathable gas may comprise, for example, one or more of a flow rate, a volume, a pressure, humidity, temperature, acceleration, velocity, and/or other gas parameters.

Transition module 52 is configured to determine the respiratory phase (e.g., inhalation, exhalation) during breathing of subject 12. The respiratory phase determinations made by module 52 are based on the output signals from sensors 18, information determined by parameter module 50, and/or other information. Transition module 52 may be configured to determine additional breathing parameters related to the respiration of subject 12. Additional breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters. The determinations made by transition module 52 may be used by control module 54 to control pressure generator 14 to control the pressurized flow of breathable gas delivered to subject 12, may be stored in electronic storage 24, and/or used for other uses. In some embodiments, transition module 52 is configured to determine the respiratory phase (e.g., inhalation, exhalation) based on changes in pressure, flow rate, and/or other parameters determined by parameter module 50.

Control module 54 is configured to control pressure generator 14 to generate the flow of gas in accordance with a positive pressure support therapy regime. In positive airway pressure support therapy the pressurized flow of gas generated by the pressure generator is controlled to replace and/or compliment a patient's regular breathing. Positive airway pressure support therapy may be used to maintain an open airway in a patient so that oxygen and carbon dioxide may be exchanged more easily, requiring little and/or no effort from the patient. By way of non-limiting example, control module 54 may control pressure generator 14 such that the pressure support provided to the subject via the flow of gas comprises continuous positive airway pressure support (CPAP), bi-level positive airway pressure support (BPAP), proportional positive airway pressure support (PPAP), forced oscillation technique, and/or other types of pressure support therapy.

CPAP supplies a fixed positive pressure to maintain a continuous level of positive airway pressure in a patient. BPAP provides a first inspiratory pressure (IPAP) and a second, typically lower, expiratory pressure (EPAP) for easier exhalation during ventilation. In some therapy modes (e.g., PPAP), control module 54 may control pressure generator 14 to apply variable pressure support in which the amount of pressure delivered to the patient during inhalation and/or during exhalation is determined and delivered on a breath by breath basis. In some embodiments, control module 54 may be configured to control pressure generator 14 to temporarily drop the supplied pressure during exhalation (C-Flex) to reduce exhalation effort required by the patent.

In some embodiments, control module 54 is configured to control pressure generator 14 to deliver staged pressure support. In staged pressure support therapy, the pressure delivered by pressure generator 14 gradually increases over time. In some embodiments, control module 54 may control pressure generator 14 to switch therapy modes based on information related to the respiration of subject 12 and/or other information. For example, control module 54 may control pressure generator 54 to change from BPAP to CPAP after a certain number of breaths by subject 12.

Control module 54 is configured to control pressure generator 14 based on information related to the output signals from sensors 18, information determined by parameter module 50, information determined by transition module 52, information entered by a user to user interface 22, and/or other information.

User interface 22 is configured to provide an interface between system 10 and subject 12 and/or other users through which subject 12 and/or other users may provide information to and receive information from system 10. Other users may comprise, for example, a caregiver, a doctor, and/or other users. This enables data, cues, results, and/or instructions and any other communicable items, collectively referred to as "information," to be communicated between a user (e.g., subject 12) and one or more of pressure generator 14, processor 20, and/or other components of system 10. For example, a user may specify one or more therapy regimes that are to be delivered to subject 12 using user interface 22. Control module 54 may then customize the therapy regime delivered to the subject based on the one or more inputs made by the user to the user interface. As another example, therapy pressures, the breath rate of subject 12, the portable power source energy level, and/or other information may be displayed to a user (e.g., subject 12) via user interface 22.

Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 22 comprises a plurality of separate interfaces. In one embodiment, user interface 22 comprises at least one interface that is provided integrally with housing 28.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, etc.).

Information determined by processor 20 and/or stored by electronic storage 24 may comprise information related to respiration of subject 12, compliance, use frequency, and/or other information. The information stored by electronic storage 24 may be viewed via user interface 22, by connecting (wired and/or wireless) to a separate computer, and/or other via other methods. The information stored by electronic storage 24 may be used, for example, to adjust settings, to make adjustments to power source 26, used by a doctor to make medical decisions, and/or for other uses. In some embodiments, system 10 may include a wireless transmitter (not shown) and the information determined by processor 20, the information stored by electronic storage 24, and/or other information may be communicated to a care giver, for example, over a wireless network. By way of a non-limiting example, the care giver may receive use information, patient status, and/or other information, allowing the care giver to remotely track the therapy delivered by system 10. By way of a second non-limiting example, system 10 may be configured to signal for emergency assistance when information determined by processor 20 related to the respiration of subject 12 breaches a threshold level.

Portable power source 26 is configured to power pressure generator 14, one or more sensors 18, one or more processors 20, user interface 22, electronic storage 24, and/or other components of system 10 in a portable manner Power source 26 may comprise one or more power sources connected in series and/or in parallel. In some embodiments, power source 26 is rechargeable. Power source 26 may be recharged via a home AC power source, a car battery outlet, an airplane power outlet, a USB port, a non-contact charging circuit, and/or other recharging methods. In some embodiments, portable power source 26 may supply up to 10V. In some embodiments, portable power source 26 may supply up to 15V. In some embodiments, portable power source 26 may supply up to 20V. Examples of portable power sources that may be included as portable power source 26 include one or more DC batteries, Lithium Ion and/or Lithium Polymer Cells, Nickel Metal Hydride, and/or other portable power sources. In some embodiments, portable power source 26 is configured to power system 10 for 10 or more hours of use. In some embodiments, portable power source 26 is configured to power system 10 for up to 10 hours of use. In some embodiments, portable power source 26 is configured to power system 10 for up to 8 hours of use. In some embodiments, portable power source 26 is configured to power system 10 for up to 6 hours of use.

Housing 28 is configured to contain pressure generator 14, subject interface 16, one or more sensors 18, one or more processors 20, user interface 22, electronic storage 24, power source 26, flow path 60, exhaust port 62, handle 30, and/or other components of system 10. Housing 28 is configured to contain the components of system 10 in a space small enough to be handheld and portable so pressure support therapy may be delivered at any time during the normal daily activities of subject 12. In some embodiments, the weight of system 10 is up to three pounds. In some embodiments, the weight of system 10 is up to two pounds. In some embodiments, the weight of system 10 is up to one pound. In some embodiments, the volume of housing 28 is up to 135 cubic inches. In some embodiments, the volume of housing 28 is up to 100 cubic inches. In some embodiments, the volume of housing 28 is up to 60 cubic inches.

Flow path 60 is configured to place subject interface 16 in fluid communication with pressure generator 14 and/or exhaust port 62. Exhaust port 62 is configured to direct exhaled gas from flow path 60 and/or pressure generator 14 to the ambient atmosphere. In some embodiments, flow through exhaust port 62 may be controlled by a valve 63. Valve 63 may be controlled by processor 20 to close during inhalation of subject 12 and open during exhalation. By way of a non-limiting example, control module 54 may control valve 63 to open and/or close based on one or more parameters determined by parameter module 50, information determined by transition module 52, and/or other information. In some embodiments, housing 28 may contain one or more additional ports (e.g., USB) configured to provide one or more connection points such that portable power source 26 may be recharged, electronic storage 24 may be accessed, and/or for other purposes.

Handle 30 is configured to be attached to and/or formed by housing 28. Handle 30 is configured to be grasped by subject 12 to hold the housing in position with respect to the airway of subject 12 as the pressurized flow of breathable gas is delivered to the airway of subject 12. Handle 30 may be attached to housing 28 by coupling handle 30 to housing 28 at one or more locations with screws and/or another method of fixing handle 30 to housing 28. Handle 30 may be formed in housing 28 by way of a ridged, knurled, and/or other textured surface. Handle 30 formed in housing 28 may comprise finger shaped surface depressions in housing 28 such that a user's fingers may fit into the finger depressions for gripping system 10. The method for mounting, and/or the form factor for handle 30 formed by housing 28 described in the present disclosure are not intended to be limiting. Handle 30 may be attached to and/or formed in housing 28 by any method, in any shape, and/or in any location(s) that allows it to function as described herein.

Figure 2:
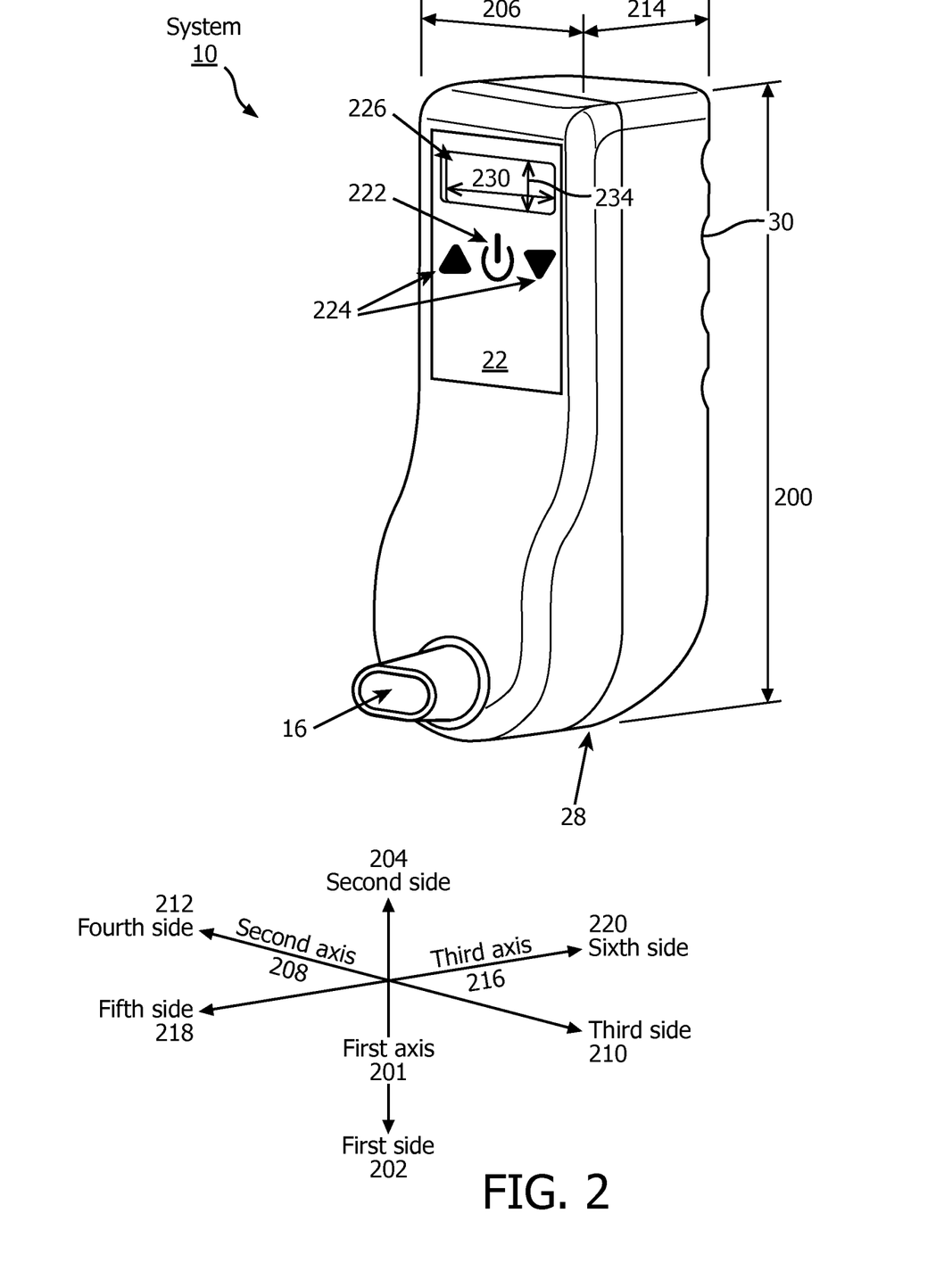
FIG. 2 is an example embodiment of the portable handheld pressure support system.

By way of a non-limiting example FIG. 2 shows a perspective view of a possible embodiment of system 10. In this embodiment, housing 28 has a length 200 running along a first axis 201 from a first side 202 to a second side 204 of less than about 7 inches. Length 200 may be between about 5 inches and about 7 inches. Length 200 may be about 6 inches. In some embodiments, housing 28 may have a width 206 running along a second axis 208 from a third side 210 to a fourth side 212 of greater than about 3 inches. Width 206 may be between about 2 inches and about 3 inches. Width 206 may be about 2.5 inches. Housing 28 has a thickness 214 running along a third axis 216 from a fifth side 218 toward a sixth side 220 of less than about 5 inches. Thickness 214 may be between about 4 inches and about 5 inches. Thickness 214 may be about 4.5 inches. The generally rectangular shape and approximate dimensions of housing 28 shown in FIG. 2 are not intended to be limiting. Housing 28 may take any shape that allows it to function as described in the present disclosure.

User interface 22 is also shown in FIG. 2. In example FIG. 2, user interface 22 is located on fifth side 218 and includes a power button 222, adjustment buttons 224, and a display 226. In this embodiment, display 226 has a width 230 running along second axis 208 from third side 210 to fourth side 212 of greater than about 2 inches. Width 230 may be between about 1 inch and about 2 inches. Width 230 may be about 1.8 inches. Display 226 has a height 234 running along first axis 201 from first side 202 toward second side 204 of greater than about 0.5 inches. Height 234 may be between about 0.5 inches and about 1 inch. Height 234 may be about 0.6 inches.

Examples of subject interface 16 and handle 30 are also shown in FIG. 2. In FIG. 2, handle 30 is formed in housing 28 on sixth side 220 toward second side 204, opposite user interface 22. In FIG. 2, subject interface 16 is located on fifth side 218 (the same side as user interface 22) toward first side 202. Subject interface 16 is located in an area where thickness 214 increases along third axis toward fifth side 218 near first side 202.

Figure 3:
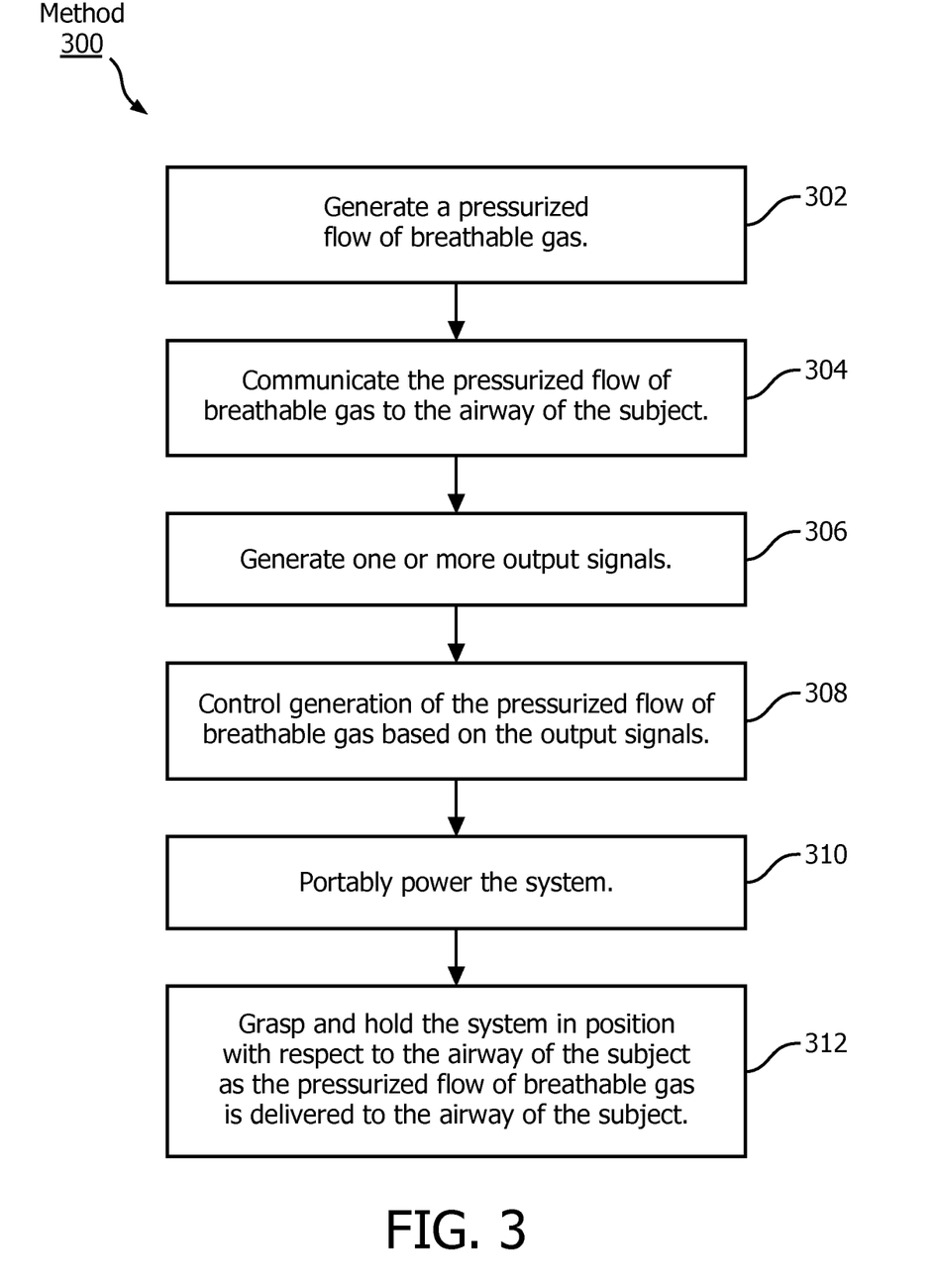
FIG. 3 is a method of delivering a pressurized flow of breathable gas to the airway of a subject.

FIG. 3 illustrates a method 300 of delivering a pressurized flow of breathable gas to the airway of a subject with a handheld pressure support system that includes a housing. The housing contains a pressure generator, a subject interface, one or more sensors, one or more processors, and a power source. The housing forms and/or is attached to a handle. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, the pressurized flow of breathable gas is generated with the pressure generator. In some embodiments, operation 302 is performed by a pressure generator the same as or similar to pressure generator 14 (shown in FIG. 1 and described herein).

At an operation 304, the pressurized flow of breathable gas is communicated to the airway of the subject with the subject interface. In some embodiments, operation 304 is performed by a subject interface the same as or similar to subject interface 16 (shown in FIG. 1 and described herein).

At an operation 306, one or more output signals conveying information related to one or more gas parameters of the pressurized flow of breathable gas are generated with the one or more sensors. In some embodiments, operation 306 is performed by sensors the same as or similar to sensors 18 (shown in FIG. 1 and described herein.)

At an operation 308, the generation of the pressurized flow of breathable gas is controlled with the one or more processors. The generation of the pressurized flow of breathable gas is controlled based on the output signals, according to a positive pressure support therapy regime. In some embodiments, operation 308 is performed by a processor the same as or similar to processor 20 (shown in FIG. 1 and described herein.)

At an operation 310, the pressure generator, the one or more sensors, and the one or more processors are powered with the portable power source. In some embodiments, operation 310 is performed by a portable power source the same as or similar to power source 26 (shown in FIG. 1 and described herein.)

At an operation 312, the handle is grasped to hold the housing in position with respect to the airway of the subject as the pressurized flow of breathable gas is delivered to the airway of the subject. In some embodiments, operation 312 is performed by a handle the same as or similar to handle 30 (shown in FIG. 1 and described herein.)

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A portable handheld pressure support system configured to deliver a pressurized flow of breathable gas to the airway of a subject, the pressure support system comprising:
    a pressure generator configured to generate the pressurized flow of breathable gas;
    a subject interface configured to communicate the pressurized flow of breathable gas to the airway of the subject, the subject interface comprising a conduit, a filter, and a mouthpiece, the filter and the mouthpiece configured to removably couple with the conduit;
    one or more sensors configured to generate output signals conveying information related to one or more gas parameters of the pressurized flow of breathable gas;
    one or more processors configured to control operation of the pressure generator to generate the pressurized flow of breathable gas based on the output signals from the one or more sensors, according to a positive pressure support therapy regime, wherein the one or more processors are configured to control the pressure generator to automatically switch from the positive pressure support therapy regime to a different positive pressure support therapy regime based on the output signals from the one or more sensors indicating that the subject has taken a certain number of breaths;
    a portable power source configured to power the pressure generator, the one or more sensors, and the one or more processors;
    a housing configured to contain the pressure generator, the subject interface, the one or more sensors, the one or more processors, and the power source; and
    a handle formed in a wall of the housing configured to be grasped by the subject to hold the housing in position with respect to the airway of the subject as the pressurized flow of breathable gas is delivered to the airway of the subject such that the subject interface comprising the conduit, the filter, and the mouthpiece is in position to be engaged by the mouth of the subject.

2. The system of claim 1, wherein the maximum volume of the housing is 135 cubic inches.

3. The system of claim 1, wherein the positive pressure support therapy regime and the different positive pressure support therapy regime comprise different ones of non-invasive ventilation: continuous positive airway pressure support, proportional positive airway pressure support, or bi-level positive airway pressure support.

4. The system of claim 1, wherein the power source is rechargeable via a USB port.

5. The system of claim 1, further comprising:
    a user interface configured to provide an interface between the system and a user through which the user provides information to and receives information from the system, wherein the one or more processors customize the therapy regime delivered to the subject based on one or more inputs made by the user to the user interface, wherein the user interface is powered by the power source and contained in the housing, and wherein the user interface is located on a second wall of the housing that also includes the subject interface, the second wall being opposite the wall of the housing with the handle such that the user interface is viewable by the subject when the housing is in position with respect to the airway of the subject as the pressurized flow of breathable gas is delivered to the airway of the subject.

6. The system of claim 5, wherein the user interface is configured to (1) receive input specifying the positive pressure support therapy regime and the different positive pressure support therapy regime, and (2) display therapy pressures, a breath rate of the subject, and a portable power source energy level.

7. The system of claim 1, wherein a maximum volume of the housing is 60 cubic inches and the system has a weight of up to one pound.

8. The system of claim 1, wherein the one or more processors are configured to control the operation of the pressure generator by:
    determining the one or more gas parameters of the pressurized flow of breathable gas based on the output signals;
    determining a respiratory phase during breathing of the subject based on the one or more gas parameters; and
    controlling the operation of the pressure generator to generate the pressurized flow of breathable gas based on the one or more gas parameters and the respiratory phase, according to the positive pressure support therapy regime,
    wherein controlling the operation of the pressure generator to generate the pressurized flow of breathable gas based on the one or more gas parameters and the respiratory phase, according to the positive pressure support therapy regime, comprises temporarily dropping a supplied pressure during exhalation to reduce exhalation effort required by the subject.

9. A method of delivering a pressurized flow of breathable gas to the airway of a subject with a handheld pressure support system that includes a housing, the housing containing a pressure generator, a subject interface, one or more sensors, one or more processors, a power source, and a handle formed in a wall of the housing, the method comprising:
    generating the pressurized flow of breathable gas with the pressure generator;

communicating the pressurized flow of breathable gas to the airway of the subject with the subject interface, the subject interface comprising a conduit, a filter, and a mouthpiece, the filter and the mouthpiece configured to removably couple with the conduit;

generating output signals conveying information related to one or more gas parameters of the pressurized flow of breathable gas with the one or more sensors;

controlling generation of the pressurized flow of breathable gas with the one or more processors, based on the output signals, according to a positive pressure support therapy regime, wherein the one or more processors are configured to control the pressure generator to automatically switch from the positive pressure support therapy regime to a different positive pressure support therapy regime based on the output signals from the one or more sensors indicating that the subject has taken a certain number of breaths;

portably powering the pressure generator, the one or more sensors, and the one or more processors with the power source; and facilitating grasping of the handle to hold the housing in position with respect to the airway of the subject as the pressurized flow of breathable gas is delivered to the airway of the subject such that the subject interface comprising the conduit, the filter, and the mouthpiece is in position to be engaged by the mouth of the subject.

10. The method of claim 9, wherein the maximum volume of the housing is 135 cubic inches.

11. The method of claim 9, wherein the positive pressure support therapy regime and the different positive pressure support therapy regime comprise different ones of non-invasive ventilation: continuous positive airway pressure support, proportional positive airway pressure support, or bi-level positive airway pressure support.

12. The method of claim 9, wherein the power source is rechargeable via a USB port.

13. The method of claim 9, further comprising:
interfacing between the pressure generator, the one or more sensors, the one or more processors, and/or the power source and a user with a user interface, through which the user provides information to and receives information from the pressure generator, the one or more sensors, the one or more processors, and/or the power source;
customizing the therapy regime delivered to the subject based on one or more inputs made by the user to the user interface,
powering the user interface with the power source; and
containing the user interface in the housing, wherein the user interface is located on a second wall of the housing that also includes the subject interface, the second wall being opposite the wall of the housing with the handle such that the user interface is viewable by the subject when the housing is in position with respect to the airway of the subject as the pressurized flow of breathable gas is delivered to the airway of the subject.

14. The method of claim 13, wherein the method further comprises (1) receiving, with the user interface, input specifying the positive pressure support therapy regime and the different positive pressure support therapy regime, and (2) displaying, with the user interface, therapy pressures, a breath rate of the subject, and a portable power source energy level.

15. The method of claim 9, wherein a maximum volume of the housing is 60 cubic inches and the system has a weight of up to one pound.

16. The method of claim 9, wherein controlling generation of the pressurized flow of breathable gas comprises:
determining, with the one or more processors, the one or more gas parameters of the pressurized flow of breathable gas based on the output signals;
determining, with the one or more processors, a respiratory phase during breathing of the subject based on the one or more gas parameters; and
controlling, with the one or more processors, the operation of the pressure generator to generate the pressurized flow of breathable gas based on the one or more gas parameters and the respiratory phase, according to the positive pressure support therapy regime,
wherein controlling the operation of the pressure generator to generate the pressurized flow of breathable gas based on the one or more gas parameters and the respiratory phase, according to the positive pressure support therapy regime, comprises temporarily dropping a supplied pressure during exhalation to reduce exhalation effort required by the subject.

17. A portable handheld pressure support system configured to deliver a pressurized flow of breathable gas to the airway of a subject, the pressure support system comprising:
means for generating the pressurized flow of breathable gas;
means for communicating the pressurized flow of breathable gas to the airway of the subject, the means for communicating comprising a conduit, a filter, and a mouthpiece, the filter and the mouthpiece configured to removably couple with the conduit;
means for generating output signals conveying information related to one or more gas parameters of the pressurized flow of breathable gas;
means for controlling the means to generate the pressurized flow of breathable gas based on the output signals, according to a positive pressure support therapy regime, wherein the means for controlling are configured to control the means for generating the pressurized flow of breathable gas to automatically switch from the positive pressure support therapy regime to a different positive pressure support therapy regime based on the output signals from the means for generating output signals indicating that the subject has taken a certain number of breaths;
means for portably powering the means to generate the pressurized flow of breathable gas, the means for generating output signals, and the means for controlling;
means for containing the means to generate the pressurized flow of breathable gas, the means for communicating, the means for generating output signals, the means for controlling, and the means for portably powering; and
means for engaging the hand of the subject to be grasped by the subject, the means for engaging being formed in a wall of the means for containing, the means for engaging being configured to be grasped by the subject to hold the means for containing in position with respect to the airway of the subject as the pressurized flow of breathable gas is delivered to the airway of the subject such that the means for communicating comprising the conduit, the filter, and the mouthpiece is in position to be engaged by the mouth of the subject.

18. The system of claim 17, wherein the maximum volume of the means for containing is 135 cubic inches.

19. The system of claim 17, wherein the positive pressure support therapy regime and the different positive pressure support therapy regime comprise different ones of non-invasive ventilation: continuous positive airway pressure support, proportional positive airway pressure support, or bi-level positive airway pressure support.

20. The system of claim 17, wherein the means for portably powering is rechargeable via a USB port.

21. The system of claim 17, further comprising means for interfacing between the system and a user through which the user provides information to and receives information from the system, wherein the means for controlling customizes the therapy regime delivered to the subject based on one or more inputs made by the user to the means for interfacing, wherein the means for interfacing is powered by the means for portably powering and contained in the means for containing, and wherein the means for interfacing is located on a second wall of the housing that also includes the means for communicating, the second wall being opposite the wall of the means for containing with the means for engaging such that the means for interfacing is viewable by the subject when the means for containing is in position with respect to the airway of the subject as the pressurized flow of breathable gas is delivered to the airway of the subject.

22. The system of claim 21, wherein the means for interfacing is configured to (1) receive input specifying the positive pressure support therapy regime and the different positive pressure support therapy regime, and (2) display therapy pressures, a breath rate of the subject, and an energy level of the means for portably powering.

23. The system of claim 17, wherein a maximum volume of the means for containing is 60 cubic inches and the system has a weight of up to one pound.

24. The system of claim 17, wherein the means for controlling the means to generate the pressurized flow of breathable gas comprises:
- means for determining the one or more gas parameters of the pressurized flow of breathable gas based on the output signals;
- means for determining a respiratory phase during breathing of the subject based on the one or more gas parameters; and
- means for controlling the operation of the means to generate the pressurized flow of breathable gas based on the one or more gas parameters and the respiratory phase, according to the positive pressure support therapy regime,
- wherein controlling the operation of the means to generate the pressurized flow of breathable gas based on the one or more gas parameters and the respiratory phase, according to the positive pressure support therapy regime, comprises temporarily dropping a supplied pressure during exhalation to reduce exhalation effort required by the subject.

* * * * *